United States Patent
O'Neill et al.

(10) Patent No.: US 10,531,813 B2
(45) Date of Patent: Jan. 14, 2020

(54) COLLECTING AND PROCESSING RELIABLE ECG SIGNALS AND GATING PULSES IN A MAGNETIC RESONANCE ENVIRONMENT

(71) Applicant: KONINKLIJKE PHILIPS N.V., Eindhoven (NL)

(72) Inventors: Francis Patrick O'Neill, Kissimmee, FL (US); Eduardo Mario Rey, Orlando, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 250 days.

(21) Appl. No.: 15/105,213

(22) PCT Filed: Jan. 12, 2015

(86) PCT No.: PCT/IB2015/050210
§ 371 (c)(1),
(2) Date: Jun. 16, 2016

(87) PCT Pub. No.: WO2015/107443
PCT Pub. Date: Jul. 23, 2015

(65) Prior Publication Data
US 2016/0310037 A1    Oct. 27, 2016

Related U.S. Application Data

(60) Provisional application No. 61/928,624, filed on Jan. 17, 2014.

(51) Int. Cl.
*A61B 5/055* (2006.01)
*A61B 5/0408* (2006.01)
(Continued)

(52) U.S. Cl.
CPC ............ *A61B 5/055* (2013.01); *A61B 5/0402* (2013.01); *A61B 5/0408* (2013.01);
(Continued)

(58) Field of Classification Search
CPC ............ A61B 5/04082; A61B 5/04085; A61B 5/0402; A61B 5/04012; A61B 5/0408;
(Continued)

(56) References Cited

U.S. PATENT DOCUMENTS 4,577,639 A    3/1986 Simon
6,032,063 A    2/2000 Hoar
(Continued)

FOREIGN PATENT DOCUMENTS

EP    1275342         1/2003
EP    2614769 A1 *   7/2013    ........... A61B 5/7203
(Continued)

*Primary Examiner* — Eun Hwa Kim (57) ABSTRACT

An electrocardiogram (ECG) electrode patch (10) system (50) for use in a magnetic resonance (MR) environment includes a flexible patch material (12) configured for attachment to human skin, and a plurality of electrodes (20). The electrodes (20) Care attached to the patch material (12) and configured to sense a plurality of ECG signals with different amplitudes across pairs of electrodes in at least two different directions.

13 Claims, 4 Drawing Sheets

(51) Int. Cl.
*A61B 5/00* (2006.01)
*A61B 5/0402* (2006.01)

(52) U.S. Cl.
CPC .......... *A61B 5/04085* (2013.01); *A61B 5/683* (2013.01); *A61B 5/6833* (2013.01); *A61B 5/7289* (2013.01); *A61B 2562/0215* (2017.08)

(58) Field of Classification Search
CPC ... A61B 5/6822; A61B 5/6831; A61B 5/6832; A61B 5/6833; A61B 5/68335; A61B 5/055; A61B 5/7289; A61B 5/7221; A61B 2562/0215
See application file for complete search history.

(56) References Cited

U.S. PATENT DOCUMENTS

| | | | |
|---|---|---|---|
| 6,052,614 A | 4/2000 | Morris | |
| 7,215,989 B1* | 5/2007 | Burks | A61B 5/04085 600/391 |
| 8,019,402 B1* | 9/2011 | Kryzpow | A61B 5/04085 600/386 |
| 8,494,620 B2 | 7/2013 | Rey | |
| 8,706,215 B2 | 4/2014 | Kaib | |
| 2003/0010339 A1 | 1/2003 | Banner et al. | |
| 2004/0225210 A1* | 11/2004 | Brosovich | A61B 5/0428 600/372 |
| 2007/0221221 A1 | 9/2007 | Cooke et al. | |
| 2008/0249389 A1 | 10/2008 | Haug | |
| 2008/0281180 A1 | 11/2008 | Choe | |
| 2009/0270715 A1 | 10/2009 | Demharter | |
| 2009/0270716 A1 | 10/2009 | Demharter | |
| 2010/0071696 A1 | 3/2010 | Jafari | |
| 2011/0025429 A1* | 2/2011 | Syal | H01P 3/081 333/34 |
| 2011/0082359 A1* | 4/2011 | Rey | A61B 5/04028 600/393 |
| 2011/0237970 A1 | 9/2011 | Isaza | |
| 2011/0288605 A1 | 11/2011 | Kaib et al. | |
| 2014/0364716 A1* | 12/2014 | Smink | A61B 5/6892 600/393 |

FOREIGN PATENT DOCUMENTS

| | | |
|---|---|---|
| JP | 2007202905 | 8/2007 |
| JP | 2008000436 A | 1/2008 |
| WO | 2013/175457 | 11/2013 |

\* cited by examiner

COLLECTING AND PROCESSING RELIABLE ECG SIGNALS AND GATING PULSES IN A MAGNETIC RESONANCE ENVIRONMENT

CROSS REFERENCE TO RELATED APPLICATIONS

This application is the U.S. National Phase application under 35 U.S.C. § 371 of International Application No. PCT/IB2015/050210, filed Jan. 12, 2015, published as WO 2015/107443 on Jul. 23, 2015, which claims the benefit of U.S. Provisional Patent Application No. 61/928,624 filed Jan. 17, 2014. These applications are hereby incorporated by reference herein.

The following relates generally to physiological signal monitoring in a magnetic resonance environment. It finds particular application in conjunction with electrocardiography (ECG) in magnetic resonance imaging, and will be described with particular reference thereto. However, it will be understood that it also finds application in other usage scenarios and is not necessarily limited to the aforementioned application.

Electrocardiography (ECG) monitoring measures heart activity through electrical activity sensed by electrodes affixed to the skin of a subject. Electrical impulses generated by the polarization and depolarization of cardiac tissue are sensed by the electrodes which are converted into a waveform. The visible waveform typically includes a P-wave, a Q-R-S wave complex, and a T-wave. The QRS complex represents the rapid depolarization of the ventricles, which are the largest muscles and therefore present the largest amplitude.

ECG monitoring is performed during magnetic resonance imaging (MRI) to monitor patient vital signs and/or to gate data acquisition. Gating is typically used in MRI to time and/or adjust acquisition to remove motion artifacts. The ECG signal provides the timing of the heart motion, which can then be used to adjust the acquisition to compensate for the motion of the heart and/or subsequent effect on tissues the body, e.g. blood pulse.

In MRI, strong magnetic fields and radio frequency (RF) pulses are applied to a subject to excite, manipulate, and encode resonance in the tissues of the subject. The same magnetic fields and RF pulses generate electrical currents in the body and any object used to sense and receive the signals, such as eddy currents. The generated currents add noise to the ECG signals. The generated currents can create patient safety issues, such as electrical burns.

Electrodes typically used in MRI applications are placed in close proximity to each other, which differs from ECG electrodes used outside the MRI environment. The close proximity to each other reduces the noise from the induced body currents, but also reduces the amplitude of the sensed signals. To further improve the signal, various filters are applied such as slew rate, band pass, and t-suppression. The filters are applied to the composite waveform or to a lead serially, e.g. one lead at a time. With closely placed electrodes, the misplacement by even a fraction of an inch on the skin of the subject can cause excessive noise or result in a signal amplitude too small in a lead to process. Unitary patches are typically used to guide and direct the placement of electrodes to reduce misplacement. Unitary patches, such as a square, cluster the electrodes closely and are labeled for placement on the skin of the chest typically using the breast bone and nipples of the breast as points of reference.

ECG lead selection is often used for gating. Gradient magnetic fields are applied in different directions during MM scans. In some scans, the applied gradient fields can add noise to one or more leads which obscures the ECG lead signal, which means that a lead selected for gating with an obscured signal results in a lost scan and valuable clinical time. The various lead signals are reviewed, an alternative lead with an acceptable signal is manually selected, and a new scan is initiated with the alternatively selected lead.

The following discloses a new and improved method and apparatus for collecting and processing reliable ECG signals and gating pulses in a magnetic resonance environment which addresses the above referenced issues, and others.

In accordance with one aspect, an electrocardiogram (ECG) electrode patch system for use in a magnetic resonance (MR) environment includes a flexible patch material configured for attachment to human skin, and a plurality of electrodes. The electrodes are attached to the patch material and configured to sense a plurality of ECG signals with different amplitudes across pairs of electrodes in at least two different directions.

In accordance with another aspect, a method of using an electrocardiogram (ECG) electrode patch in a magnetic resonance environment includes affixing the ECG electrode patch to skin of a patient. The patch includes a flexible patch material configured for attachment to human skin, and a plurality of electrodes attached to the patch material and configured to sense a plurality of ECG signals with different amplitudes across pairs of electrodes in at least two different directions.

In accordance with another aspect, a system of processing electrocardiogram (ECG) signals in a magnetic resonance environment includes an ECG electrode patch, a field programmable gate array, and one or more processors. The ECG electrode patch includes a flexible patch material, four electrodes, and four electrically conductive traces. The flexible patch material is shaped with a center section and four lobes extending away from a center axis of the center section, and configured for attachment to human skin. The four electrodes are disposed in a rectilinear arrangement, each attached to one of the lobes of the patch material and configured to sense electrical activity of a heart. The four electrically conductive traces are disposed on the patch material, each trace connected to one electrode and to a common connector edge of the patch material. The field programmable gate array is programmed to filter noise simultaneously from each of a plurality of ECG lead signals and each ECG lead measuring an electrical ECG lead signal between two of the electrodes. The one or more processors is configured to detect the filtered ECG lead signal on each lead, score each detected ECG lead signal, select one of the scored ECG lead signals, and output the selected ECG lead signal.

One advantage is reliable ECG signals for monitoring and gating pulses in MRI applications.

Another advantage resides in a unitary patch which accommodates various chest shapes with proper electrode placement.

Another advantage resides in parallel processing of lead signals with different amplitudes.

Another advantage resides in automated and dynamic lead selection.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
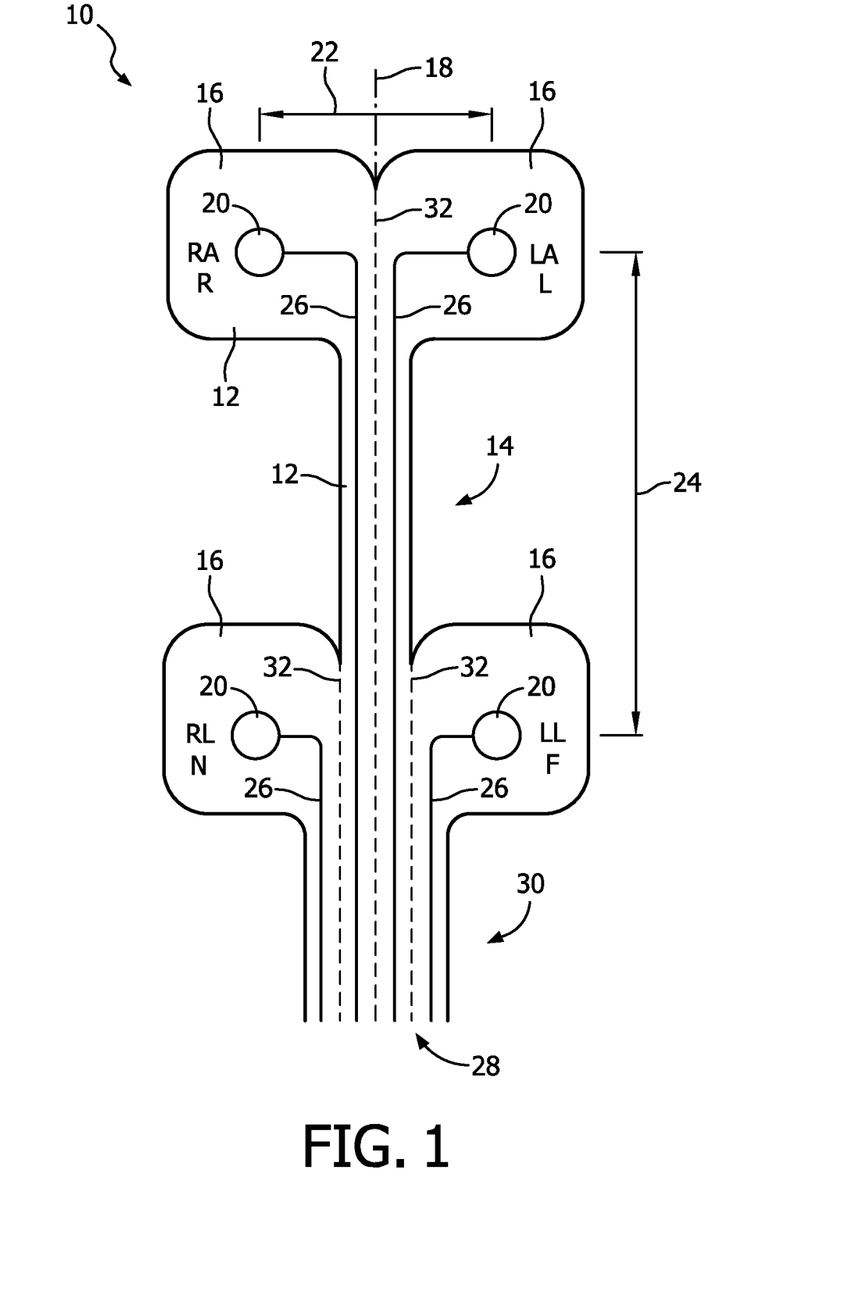
FIG. 1 schematically illustrates an embodiment of a rectilinear 4 lead ECG electrode patch.

With reference to FIG. 1, an embodiment of a rectilinear 4 lead ECG electrode patch 10 is schematically illustrated. The ECG electrode patch 10 includes a flexible patch material 12 or substrate shaped with a rectangular center 14 and four lobes 16 extending symmetrically away from a center axis 18 of the rectangular center. The patch material 12 can be made of plastic or polymer layers, and is configured for attachment to human skin. For example, an adhesive coating layer provides for attachment. The patch material shape in one embodiment is shaped a dog bone shape. The patch material can include markings for orientation, such as R, L, N, F, or RA, LA, RL, LL, etc. In other embodiments, the lobes include different sizes. For example, the lobes on one side can be extended in length or distance away from the rectangular center.

The patch 10 includes four electrodes 20 disposed in a rectilinear arrangement. Each electrode 20 is attached to or formed in one of the lobes 16 of the patch material 12 and senses electrical activity of a heart. The electrodes can include Ag—AgCl based electrodes or alternative materials such as described in patent application, "Magnetic Resonance Safe Electrode for Biopotential Measurements," Ser. No. 61/739,751, e.g. printed electrodes. The ratio of a distance 22 between electrodes on opposite sides of the center axis 18 and a distance 24 between electrodes on a same side is greater than 1.5. In one embodiment, the distance 24 between electrodes on a same side of the center axis 18 is greater than the distance 22 of electrodes on opposite sides.

The patch includes four electrically conductive traces 26 disposed on the patch material, such as conductive resistive carbon based traces. Each trace 26 connects to one electrode 20 and to a common edge 28 of the patch material 12. The traces 26 extend parallel the center axis 18 of the patch material. The patch material can include an extension 30 which extends along the central axis and the extension 30 includes the conductive traces common edge 28. The resistances of the traces are matched. For example, the resistance of traces 26 measured from the electrodes 20 to the common edge 28 are tuned to the same resistance. The resistance can be tuned in individual traces with fine longitudinal cuts in the trace, e.g. laser cuts. The cuts increase the resistance. The cuts reduce the eddy currents in the trace. The resistance can also be effected by altering the composition of the trace material.

The patch material 12 can include perforations 32 overlying or parallel to the center axis 18 and between traces 26. The perforations 32 are configured to separate at least two lobes 16 and the corresponding electrodes 20. For example, a healthcare practitioner can separate or tear the patch material along the perforations. The perforations add flexibility to the arrangement to address body contours and electrode placement without changing the matched resistance of the traces. The perforations can extend partially or fully along the patch material. The patch material perforations include perforations between traces. For example, the healthcare practitioner grasps the patch material of two lobes on opposite sides of the center axis and separates the lobes with the corresponding electrodes and connected traces to increase the distance between two of the electrodes increasing signal amplitude and noise.

Figure 2:
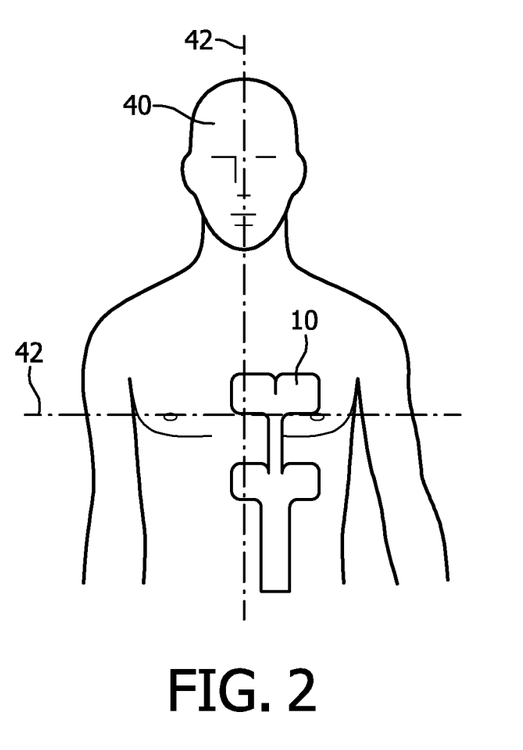
FIG. 2 diagrammatically illustrates an exemplary placement of an embodiment of the rectilinear 4 lead ECG electrode patch on a patient.

With reference to FIG. 2, an exemplary placement of an embodiment of the rectilinear 4 lead ECG electrode patch 10 attached to a patient 40 is diagrammatically illustrated. The patch 10 includes the flexible patch material shaped with an elongated center and four lobes extending symmetrically away from the vertical center axis. The patch includes four electrodes disposed with different spacing laterally than longitudinally. Each electrode attaches to one of the lobes and one electrically conductive trace disposed on or in the patch material. Each trace connects to one electrode and to the common connection edge of the patch material.

The patch 10 is oriented to the patient 40 longitudinally, vertically, if standing using a torso center line or breast bone 42 and horizontally using nipples of the breasts. The common connector edge of the traces is oriented toward the abdomen. The lobes on the patient right are oriented to the breast bone with the lobes distal to the common edge just above the nipple line. The lobes proximal to the common edge are guided for placement by the length of the rectangular center portion. The rectangular center portion is narrowed, elongated, and flexible to fit and adapt to the contours of different shapes in a breast area. The proximal lobes with the narrowed center portion attach without gaps in the patch material to the lower chest area. The shape of the patch material reduces potential gaps in the substrate and resulting potential gaps between the electrodes and the skin which interfere with reliable ECG signals.

Figure 3:
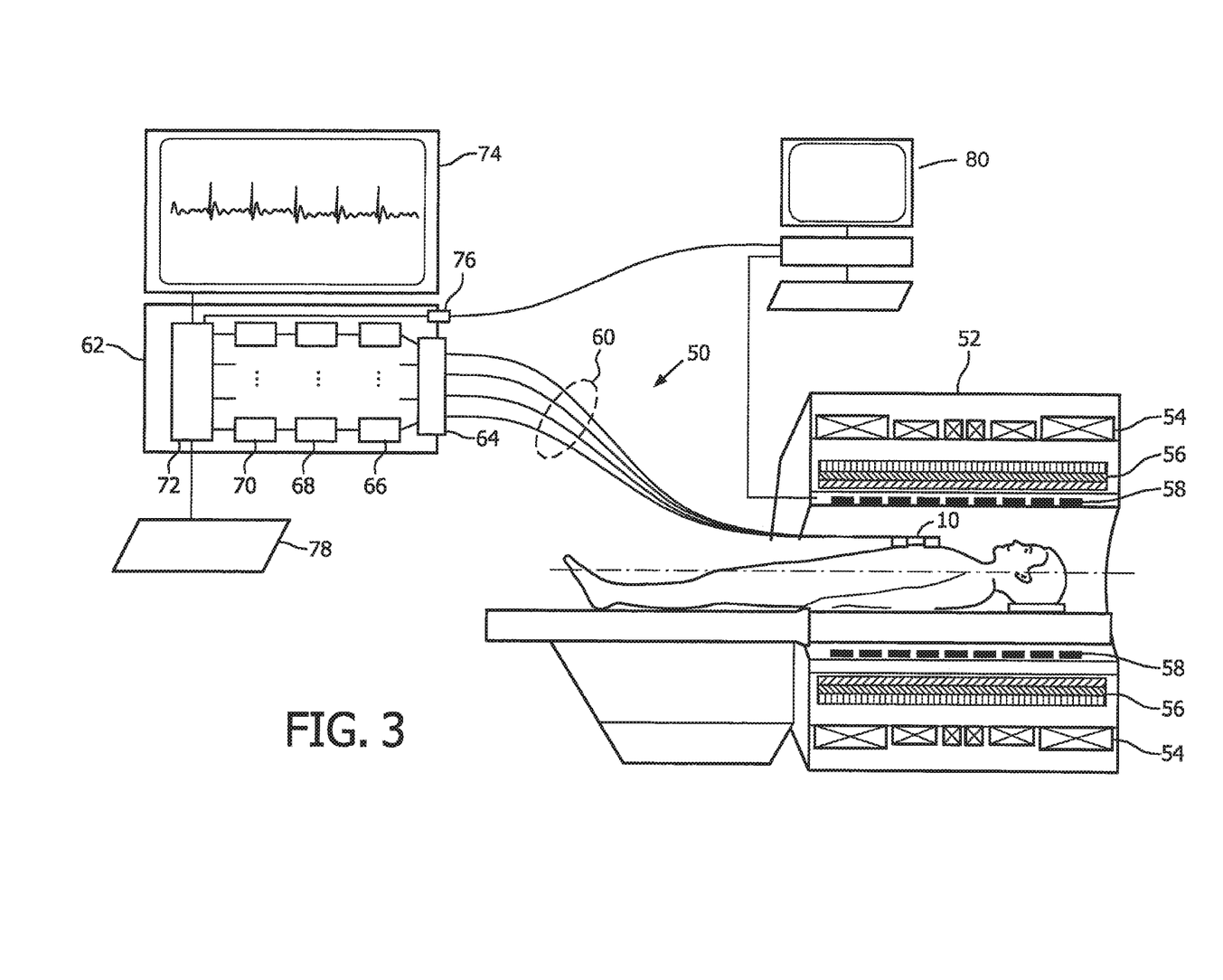
FIG. 3 schematically illustrates an embodiment of the rectilinear 4 lead ECG electrode patch with parallel lead processing system in a magnetic resonance (MR) environment.

With reference to FIG. 3, an embodiment of the rectilinear 4 lead ECG electrode patch 10 with parallel lead processing system 50 in a magnetic resonance (MR) environment is schematically illustrated. A portion of a patient 40 is located in an examining region of a magnetic resonance (MR) scanner 52, such as a horizontal bore, vertical bore, c-type, and the like. The MR scanner includes a main magnet 54 which generates a static magnetic field. The MR scanner includes one or more gradient coils 56 which generate gradient magnetic fields to manipulate and encode magnetic resonance in tissues of the patient, and one or more radio frequency (RF) coils 58 which generate RF pulses to induce magnetic resonance in the tissues of the patient.

The electrodes in the attached patch 10 sense electrical activity of the heart. The sensed electrical activity is transmitted from the electrodes to the traces to one or more cables 60 connected to the common connection edge of the patch and to an ECG monitoring device 62. The cable connects to a circuit 64 which converts the currents from the four traces to 4 ECG lead signals, e.g. lead signal I from RA and LA electrodes, lead signal II from RA and LL electrodes, etc. At least two lead signal are conveyed separately and individually to high speed noise reduction filters 66. The filters 66, such as a slew rate filter, a band pass filter, and/or a t-wave suppression filter, filter the ECG lead signals in parallel and simultaneously. Fourier analysis can be used to select frequencies with known physiological significance to be passed by the filters or frequency elements known to originate from the MR scanner and/or equipment to be blocked by the filters. The filter can include a predictive time interval filter with a learning and prediction element based on comparison with a saved ECG signal from outside the MR environment, e.g. with a computer processor or programmable gate array. The lead signals are processed in real-time. The different spacing of the electrodes in the lateral direction versus the longitudinal direction generates different amplitude ECG signals. For example, the closely space electrodes such as from lead I provide a lower amplitude, low noise signals than lead II or lead III which connect to more widely spaced electrodes.

Each filter 66 connects to a signal detection unit 68 which applies an ECG signal detection algorithm, such as a QRS wave detection algorithm to the filtered signal. Each signal detection unit 68 detects one ECG signal in one filtered ECG lead in parallel to the other signal detection units. Each signal detection unit 68 connects to a signal scoring unit 70 which scores the detected signal. The signal detection and scoring units can share the programmable components. For example, a root mean square (RMS) analysis provides a measure of signal qualities. The signal scoring can include information concerning the application for the ECG signal. For example, to create a gating or trigger pulse for MR data acquisition, the scoring can focus on finding the lead with the cleanest or most identifiable peak R wave, the QRS wave complex, or other large waveform. In another example, the scoring can look at one or more of the ECG signal waveforms, such as the p-wave, QRS-complex, t-wave, u-wave and/or combinations to identify the lead with the truest overall ECG waveform. The scoring can include directions of ECG waveforms of the heart in a direction orthogonal to the applied gradient fields which typically suffer less noise degradation from the applied MR gradient field. The filters can be embodied in a programmed field programmable gate array.

A signal selection unit 72 connects to the signal scoring units 70 and selects one of the scored ECG leads according to the scoring and outputs the selected ECG lead signal. The signal selection and signal scoring units can share programmable components. The signal selection unit can output the selected or a plurality of the ECG lead signals to a display device 74 which displays a corresponding human readable ECG waveform. The signal selection unit can receive MR cycle information via a connector 76 from the MR unit. The MR cycle information provides a basis for the selection unit to select the lead orthogonal an MR gradient as the MR gradient is applied and switch back to the lead selected when no MR gradients are being applied. Other signal selections based on the timing of the applied MR sequences are also contemplated.

During set-up, the display device 74 can display a plurality of lead signals for manual selection. The healthcare practitioner reviews the displayed lead signals and manually selects one using one or more input devices 78, such as one or more of a mouse, a keyboard, a touch screen display, one or more buttons, one or more switches, one or more toggles, and the like.

The connector 76 also conveys the selected gating ECG signal, e.g. the signal with the most distinct R-wave to the input of a gating processor or unit 80 which controls the acquisition of MR signal data and/or reconstructs images according to ECG signals. For example, MR sequences are applied during an imaging sequence, such that MR data is generated and collected at a preselected point in the patient's cardiac cycle. The ECG lead signals are filtered, detected, and scored in parallel, and a best lead signal for gating and the best lead signal for display are selected. The best lead signal(s) can change as the gradient fields change, and the selection dynamically switches among the lead signals, such that the best signal is continuously output or displayed.

The filters and/or the various units can be embodied in a programmed or configured one or more of a microprocessor, a microcontroller, a graphic processing unit (GPU), an application-specific integrated circuit (ASIC), a field-programmable gate array (FPGA), and the like. For example, one or more microprocessors or processors can be configured to filter a plurality of ECG lead signals, detect the ECG lead signal on the filtered leads, score each detected ECG lead signal, and automatically and continuously select the best ECG lead signal according to the scoring. The processors can output the parallel processed lead signals and/or the selected lead signal to the display device 74 and/or the output connector 76.

The disclosed filtering, detection, scoring, and selection techniques are suitably implemented using a non-transitory storage medium storing instructions (e.g., software) readable by the electronic data processing device and executable by the electronic data processing device to perform the disclosed filtering, detection, scoring, and selection techniques.

Examples of a display device include a computer monitor, a television screen, a touch screen, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, Head-mounted display, and the like.

Figure 4:
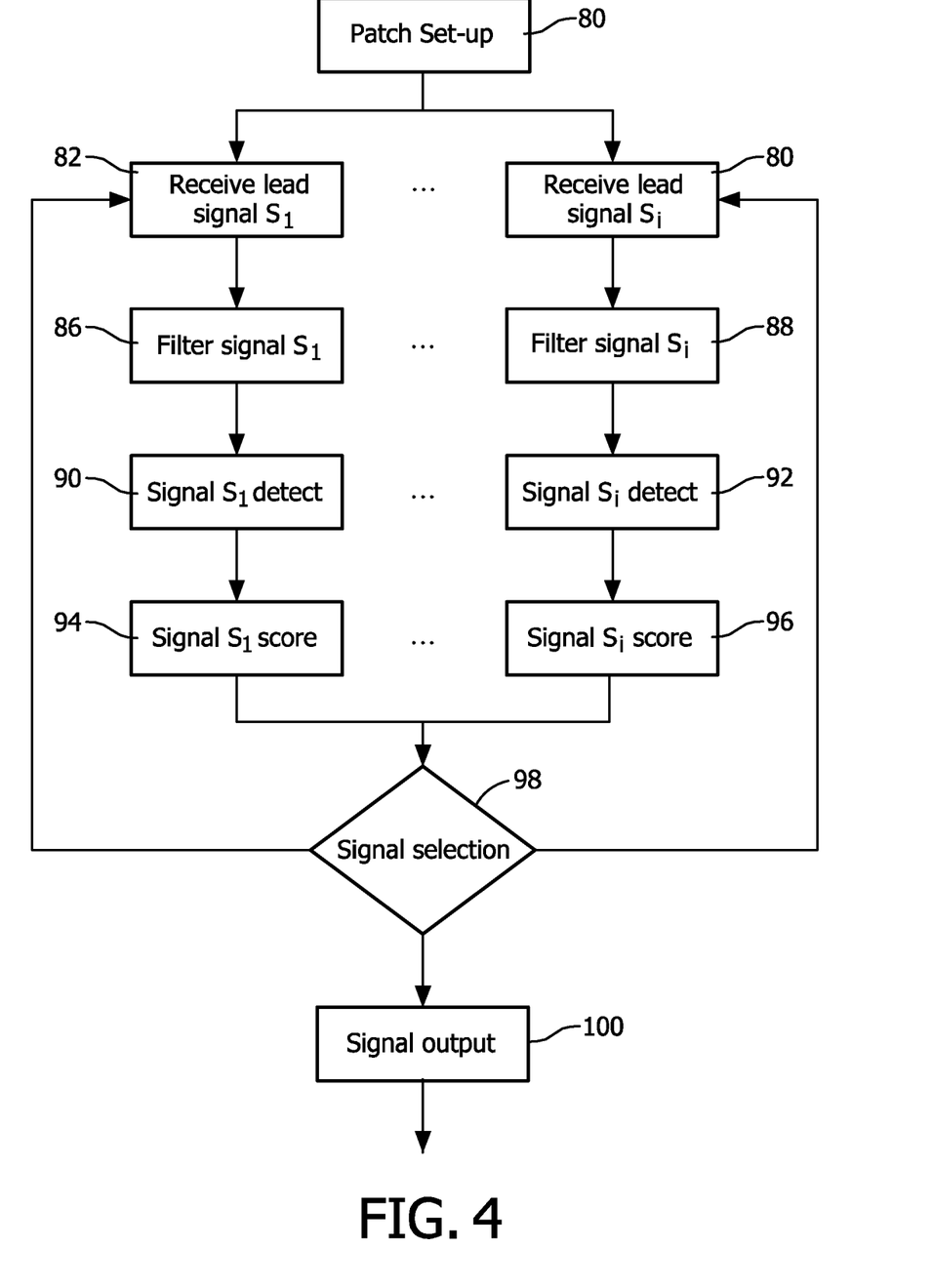
FIG. 4 flowcharts one method of using an embodiment of the rectilinear 4 lead ECG electrode in an MR environment.

With reference to FIG. 4 one method of using an embodiment of the rectilinear 4 lead ECG electrode in an MR environment is flowcharted. In a step or module 80, the ECG electrode patch 10 is affixed to skin of a patient in an orientation such as described in reference to FIG. 2. The patch 10 includes a flexible patch material shaped with a rectangular center and four lobes extending away from a center axis of the rectangular center. The patch 10 includes four electrodes disposed in a rectilinear arrangement, each attached to one of the lobes of the patch material and configured to sense electrical activity of a heart. The patch 10 includes four electrically conductive traces disposed on the patch material. Each trace connects to one electrode and to a common edge of the patch material. The attached patch can include an extension along the central axis and the extension includes the conductive traces common edge. The patch material can include perforations parallel to the central axis and between traces. The perforations are configured to separate at least two lobes and corresponding electrodes prior to attachment to the skin.

The traces connect to the ECG monitoring device 62. The traces are electrically and thermally insulated from the patient. The resistance of the traces are matched and the resistance can be tuned with longitudinal cuts which increases the resistance of the cut trace. Each lead is configured to sense electrical activity of a heart of the patient through two electrodes. The ECG monitoring device receives the ECG signals on a plurality of leads in parallel steps or modules 82, 84. Each lead is receive simultaneously.

In a step or module 86, one filter filters the received ECG signal of one lead, and simultaneously in a parallel step or module 88, a second filter filters the received ECG signal of a second lead. The filters apply a high speed noise reduction filter. Two or more leads can be filtered simultaneously or in parallel. The leads provide different amplitude ECG signals. The leads provide orthogonal vectors of heart electrical activity. The orthogonal vectors will be affected differently by applied gradient magnetic fields. For example, a lead orthogonal to a lead affected by an applied gradient field is unlikely to be affected, e.g. lead I measures vectors orthogonal to lead II or lead III. The difference in amplitude between leads is based on the ratio of a distance between electrodes on opposite sides of the center axis. A longitudinal distance between the upper and lower electrodes is greater than 1.5 times a lateral distance between the left and right side electrodes and preferably 1.5-3 times or greater. In one embodiment, the distance between electrodes on the same side of the center axis is greater than the distance of electrodes on opposite sides.

In a step or module 90, one signal detection unit 68 applies an ECG signal detection algorithm to one filtered ECG lead signal, and in a parallel step or module 92, a second signal detection unit 68 applies the ECG signal detection algorithm to a second filtered ECG lead signal. The signal detection units 68 apply the ECG signal detection to a plurality of ECG lead signals. The signal detection units detect the lead ECG signal on each lead.

The scoring units 70 score each detected ECG lead signal in parallel steps or modules 94, 96. Each lead signal is scored. The leads can be scored on multiple criteria, such as signal quality for display on a patient monitor, signal quality for triggering or gating, signal quality during application of an MR gradient applied in one or more selected directions. The selection unit 72 selects one or more of the scored ECG lead signals in a decision step or module 98.

The selected ECG lead signal is output in a step or by a module 100. The step can include displaying one or more of the lead signals on a display device. The selected signal can change dynamically as electrophysiological conditions change, gradients are applied, or the like. The step can include connection to a gating processor gating data acquisition from the MR scanner and/or reconstruction of images based on the ECG signal pulses. The step can include receiving MR cycle information, such as the timing and direction of the MR gradient fields.

The steps of receiving ECG lead signals, filtering ECG lead signals, detecting ECG lead signals, scoring ECG lead signals, selecting an ECG lead signal, and outputting ECG lead signals can include a non-transitory computer-readable storage medium carrying software which controls one or more electronic data processing devices to perform the steps. One or more microprocessors or electronic processing devices are configured to perform the steps.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. An electrocardiogram (ECG) electrode patch system for use in a magnetic resonance (MR) environment, the system comprising:
   a flexible patch including,
   four lobes disposed symmetrically on opposite sides of a central axis of the flexible patch;
   an elongated and narrowed center section connecting the four lobes with two of the four lobes disposed oppositely at one end of the elongated and narrowed center section and two other of the four lobes disposed oppositely at another end of the elongated and narrowed center section; and
   an extension section extending along the central axis from the other end of the elongated and narrowed center section, the flexible patch material being configured for attachment to human skin;
   four electrodes, each of the four electrode attached to one of the four lobes of the flexible patch in a rectilinear arrangement, wherein each of the four electrodes sense an electrical signal of a heart of the human;
   four traces disposed on the flexible patch, wherein each of the four traces are formed from a conductive resistive carbon based material having matched electrical resistance, wherein each of the four traces are connected to one of the four electrodes and extends parallel to each other along the center section to a common connector edge on the extension section;
   a circuit configured to connect with the four traces and to convert the four electrical signals of the heart to ECG signals, wherein the circuit is further configured to derive a plurality of ECG lead signals, wherein each of the plurality of ECG lead signals is derived from the ECG signals across a pair of electrodes from the four electrodes, wherein a first ECG lead signal is derived from the ECG signals across a first pair of electrodes of the four electrodes disposed in a lateral direction orthogonal to the central axis and a second ECG lead signal is derived from ECG signals across a second pair of electrodes from the four electrodes being disposed in a longitudinal direction; and
   a plurality of high speed MR noise reduction filters configured to filter frequency elements originating from the MR scanner environment from the first and second ECG lead signals simultaneously to remove MR induced noise.

2. The system according to claim 1, further including:
a plurality of parallel signal processing circuits releasably connected with the conductive resistive carbon based traces at the common connector edge and configured to process the sensed ECG signals concurrently;
a plurality of signal detection units configured to apply an ECG signal detection algorithm, each signal detection unit being configured to detect one of the ECG signals;
a plurality of signal scoring units configured to score the detected ECG signals; and
a signal selection unit configured to select one of the ECG leads according to the scoring and output the ECG signal of the selected ECG lead.

3. The system according to claim 1, wherein the flexible patch includes perforations parallel to the center axis configured to separate at least two lobes and corresponding electrodes, wherein the flexible patch perforations include perforations between the four traces.

4. The system according to claim 1, wherein at least one of the four trace includes at least one longitudinal cut which tunes the resistance of the trace such that the resistances of the four traces are matched.

5. The system according to claim 1, wherein the electrodes are mounted with a ratio of a distance between a pair of the four electrodes on opposite sides of the center axis of the flexible patch and a distance between a pair of the four electrodes on a same side is greater than 1.5.

6. The system according to claim 2, wherein the signal selection unit is configured to apply scoring criteria to select an ECG signal to be selected for at least one of:
displaying a human readable ECG waveform on a display device;
gating an MR scanner; and
having a best signal quality during application of a gradient magnetic field by the MR scanner.

7. A magnetic resonance imaging system comprising:
a magnetic resonance scanner comprising:
an examining region configured to receive a subject longitudinally;
a main magnet disposed around the examining region to generate a static magnetic field;
a plurality of gradient coils disposed around the examining region for generating magnetic; field gradients in the examining region; and
a plurality of radio-frequency coils disposed in or around the examining region;
an ECG patch configured to be attached to the subject received in the examining region for sensing electrical ECG activity of the subject disposed within the examining region, the ECG patch comprising:
a flexible patch configured to be attached to the subject, the flexible patch including:
an elongated and narrowed center section having a longitudinal central axis configured to be disposed longitudinally;
first and second lobes on opposite sides of the central axis extending from a first end of the elongated and narrowed center section;
third and fourth lobes on opposite sides of the central axis extending from a second end of the elongated and narrowed center section; and
an extension extending longitudinally from the elongated and narrowed center section beyond the third and fourth lobes;
first, second, third, and fourth electrodes each disposed on one of the four lobes of the patch in a rectilinear arrangement and configured to sense an electrical signal of a heart of the human;
four traces having electrically conductive resistive carbon material with matched electrical resistance aligned with the central axis and disposed on the elongated and narrowed center section of the flexible patch, each of the four traces connected to one of the first, second, third, and fourth electrodes and extends to a common connector edge; and
a circuit configured to connect with the four traces at the common connector edge and to convert the electrical signals of the heart from the four traces to ECG signals having different amplitudes, wherein the circuit is further configured to derive a plurality of ECG lead signals, wherein each of the plurality of ECG lead signals is derived from the ECG signals across a pair of electrodes from the four electrodes; wherein a first ECU lead signal is derived from the ECG signals across a first pair of electrodes of the four electrodes disposed in a lateral direction orthogonal to the central axis and a second ECG lead signal is derived from ECG signals across a second pair of electrodes from the four electrodes being disposed in a longitudinal direction; and wherein a ratio of 1) a longitudinal distance between the first pair of electrodes of the four electrodes in the longitudinal direction to 2) a lateral distance between the second pair of electrodes of the four electrodes in the lateral distance is greater than 1.5.

8. An electrocardiogram (ECG) patch configured to be disposed in an examining region of a magnetic resonance (MR) scanner for sensing electrical activity of the subject disposed within the examining region, the ECG patch comprising:
a flexible patch configured to be attached to the subject, wherein the flexible patch being dog bone shaped and including:
an elongated and narrowed center section extending along a center axis;
an extension defining a common connector edge; and
four lobes extending in pairs from opposite sides of the elongated and narrowed center section, the extension extending from the elongated and narrowed section beyond the at least four lobes;
a plurality of electrodes, each of the plurality of electrodes disposed on one of the lobes of the flexible patch in a rectilinear arrangement and configured to sense the electrical activity signals of a heart of the subject,
electrically conductive resistive traces having matched electrical resistance disposed on the flexible patch, each of the electrically conductive resistive traces is connected to one of the plurality of electrodes and extends parallel to the central axis along the elongated narrowed center section and to the common connector edge;
a circuit configured to connect with the traces at the common connector edge and to convert the electrical activity signals of the heart from the four traces to ECG signals having different amplitudes, wherein a first ECG lead signal is derived from the ECG signals across a first pair of electrodes from the plurality of electrodes disposed in a lateral direction orthogonal to the central axis and a second ECG lead signal is derived from the ECG signals across a second pair of electrodes from the plurality of electrodes being disposed in a longitudinal direction; and wherein a ratio of 1) a longitudinal distance between the first pair of electrodes in the longitudinal direction to 2) a lateral distance between the second pair of electrodes of in the lateral direction is greater than 1.5.

9. The ECG patch according to claim 8, further comprises a plurality of high speed MR noise reduction filters configured to filter frequency elements originating from the MR scanner environment from the first and second ECG lead signals simultaneously to remove MR induced noise.

10. The ECG patch according to claim 8, further comprises a plurality of parallel processing circuits releasably connected to the traces at the common detector edge.

11. The ECG patch according to claim 10, wherein the plurality of parallel processing circuits are configured to detect ECG signals from the first and second ECG lead signals; score the detected ECG signals, and select one of the ECG signals based on the scoring.

12. The ECG patch according to claim 11, wherein the plurality of parallel processing circuits further output the selected ECG signal to a display device for display.

13. A method comprising:
attaching the ECG patch according to claim 8 on a left side of the subject;
disposing the subject with the ECG patch attached in the examination region of the magnetic resonance scanner; and
concurrently generating a magnetic resonance image of a portion of the subject and monitoring ECG signals based on the first and second lead signals of ECG lead signals.

* * * * *